United States Patent [19]

Keller

[11] Patent Number: 4,741,205

[45] Date of Patent: May 3, 1988

[54] "V" NOTCHED INTEGRALLY SHROUDED TURBINE BLADE AND METHOD FOR DETERMINING SHROUD TIGHTNESS AND WEAR OF A CIRCULAR ARRAY OF ROTATING BLADES DISPOSED IN A ROTOR

[75] Inventor: Bobby R. Keller, Charlotte, N.C.

[73] Assignee: Westinghouse Electric Corp., Pittsburgh, Pa.

[21] Appl. No.: 946,211

[22] Filed: Dec. 22, 1986

[51] Int. Cl.$^4$ .............................................. G01M 15/00
[52] U.S. Cl. ........................................ 73/116; 415/118
[58] Field of Search .............. 73/116, 119 R; 415/118

[56] References Cited

U.S. PATENT DOCUMENTS

| | | | |
|---|---|---|---|
| 3,932,941 | 1/1976 | Ormsby | 415/118 |
| 4,189,282 | 2/1980 | Benoist et al. | 416/221 |
| 4,298,312 | 11/1981 | Mackenzie et al. | 415/118 |
| 4,326,804 | 4/1982 | Mossey | 415/118 |

Primary Examiner—Michael J. Tokar
Assistant Examiner—Robert R. Raevis
Attorney, Agent, or Firm—F. J. Baehr, Jr.

[57] ABSTRACT

Notches are placed between adjacent shroud portions of integrally shrouded rotating blades of a steam turbine forming a turbine rotor blade row generally 90° apart and a predetermined wedging force is applied to each notch to wedge adjacent shroud segments apart, the width of the gap formed is measured, recorded and compared with future measurements made after the turbine has been in service to determine wear on the shroud portions; also, a wedging force is applied to open a gap at each notch to receive a predetermined sized shim, the wedging force is relieved clamping the shim in the gap and then generally increased until the shim can be pulled from the gap by hand, the wedging force at which the shim can be pulled is recorded and compared with future similar recordings after the rotor has been in service to provide an indication of wear on the shroud portions.

12 Claims, 2 Drawing Sheets

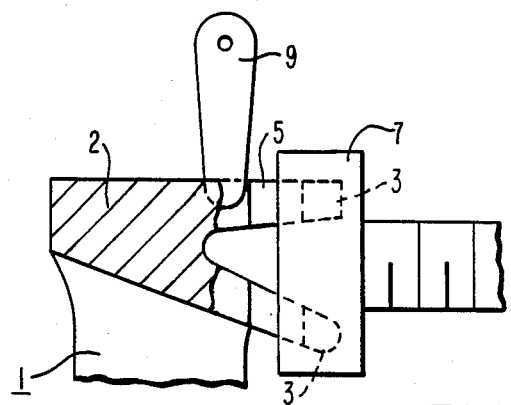
FIG. 4
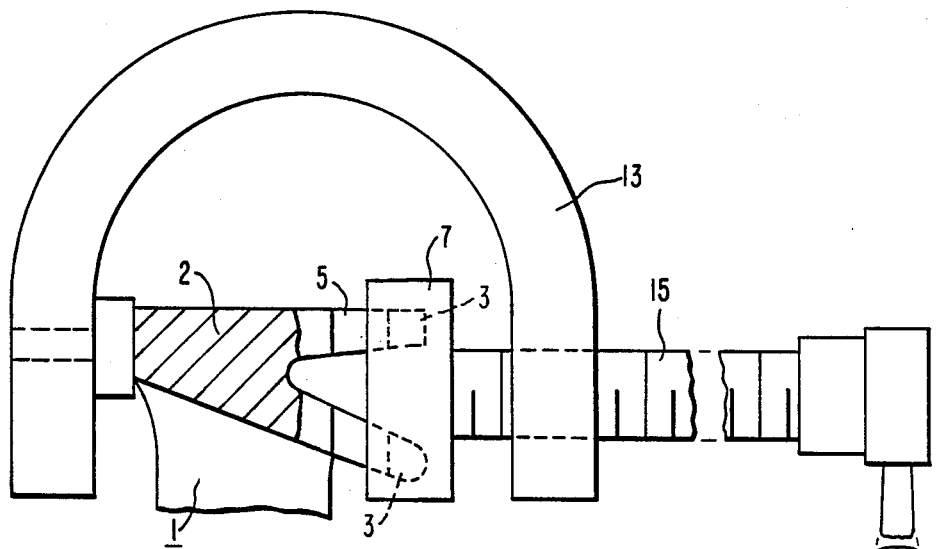
FIG. 5

"V" NOTCHED INTEGRALLY SHROUDED TURBINE BLADE AND METHOD FOR DETERMINING SHROUD TIGHTNESS AND WEAR OF A CIRCULAR ARRAY OF ROTATING BLADES DISPOSED IN A ROTOR

BACKGROUND OF THE INVENTION

This invention relates to "V" notches in integrally shrouded turbine blades and to a method of measuring the tightness of the circular array of integrally shrouded turbine blades for providing an indication of wear on the shrouds after the turbine rotor has been in service.

Integrally shrouded steam turbine blade are rotating turbine blades each of which has a shroud portion made integral therewith. These blades exhibit good vibration damping characteristics, when assembled in a turbine rotor, however, determining the tightness of a fully bladed turbine rotor of integrally shrouded blade proved difficult. Various techniques were devised and tested, but proved unsatisfactory until the method described herein was conceived and tested.

SUMMARY OF THE INVENTION

In general, a method of checking the tightness of a shroud portion of a circular array of integrally shrouded turbine blades disposed in a rotor comprises the steps of forming a notch in the shroud portion at the juncture of two blades by removing corner portions of two adjacent shroud portions; providing spreading means which register with the notch for forcing the two notched shroud portions apart to form a gap therebetween; applying a predetermined force to the spreading means to form the gap between the two notched shroud portions, and measuring and recording the width of the gap and/or spreading the adjacent blades to form a gap sufficiently wide to accept a predetermined sized shim, relieving the spreading force until the shim is clamped in the gap, then gradually increasing the spreading force until the shim can be pulled from the gap, and recording the spreading force applied as the shim can be pulled from the gap.

BRIEF DESCRIPTION OF THE DRAWINGS

The objects and advantages of this invention will become more apparent by reading the following detailed description in conjunction with the accompanying drawings, in which:

FIG. 4 is a partial sectional view of a notched blade, wedge and feeler gauge or shim utilized to measure the tightness and/or wear of the shroud portions of rotating blades installed in a rotor; and FIG. 5 is a partial sectional view showing a means for applying a force to spread adjacent notched shroud portions.

DESCRIPTION OF THE PREFERRED EMBODIMENTS

Figure 1:
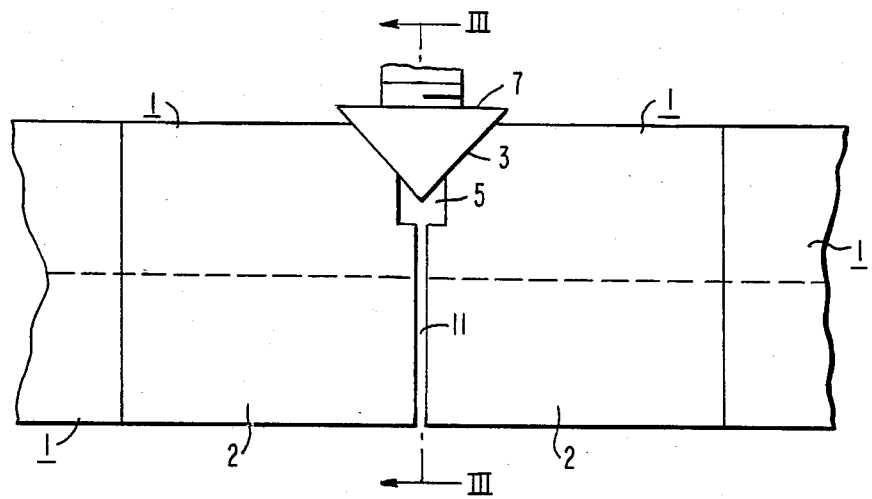
FIG. 1 is a partial plan view of a row of integrally shrouded turbine blades incorporating a notch utilized to determine the tightness of and wear on the shroud segments.

Referring now to the drawings in detail and in particular to FIG. 1 there is shown a portion of a circular array of integrally shrouded blades 1 forming a blade row of a steam turbine (not shown).

In order to determine the tightness of the circular array of integrally shrouded blade portions 2 of a row or circular array of rotating blades assembled in a turbine rotor, a "V" shaped notch 3 is cut at the juncture of two shroud portions 2 on the leading margin or side of the shroud at a predetermined included angle for example 30° by removing the adjacent corners of the shroud portions 2. Such a notch 3 is cut at predetermined intervals around the periphery of the shroud for example every 90° or four evenly spaced notches 3 per circular array or blade row. Generally the notches 3 are placed at the same location in successive blade rows. The notch 3 has a clearance portion or opening 5 cut at the apex.

Figure 2:
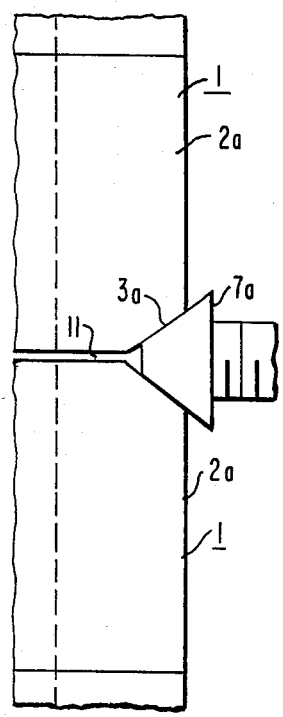
FIG. 2 is a partial plan view of an alternative notch.
Figure 3:
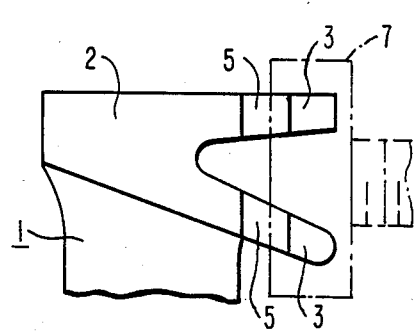
FIG. 3 is a partial sectional view taken on line III—III of FIG. 1.

A wedge 7, which registers with the "V" shaped groove, has the same inclined angle as the notch 3 and is urged into the notch 3 at some predetermined force, wedging the adjacent shroud portions 2 apart. The clearance portion 5 as shown in FIG. 1 prevents the wedge 7 from bottoming out in the notch 3. Alternatively, the wedge 7a shown in FIG. 2 registers with and engages the V-shaped notch 3a and has its apex cut away.

As shown in FIG. 4, a feeler gauge 9 is inserted about ¼ inch deep into a gap 11 formed adjacent the notch 3 by the wedging force to measure the width of the opening of the gap 11. When the measurement has been made, a shim (not shown) the same thickness as the measurement is placed in the gap and the wedging force is removed and then the same procedure is followed at the next "V" notch 3 until this procedure has been followed at each "V" notch around the periphery of the shroud. These measurements provide an indication of the tightness of the shroud and also provide a group of based measurements, which can be used with similar measurement made after the turbine has been in service and has come down for repair. By comparing the initial and subsequent measurements and indication of the wear of the shroud portions is obtained.

FIG. 5 shows a C clamp 13 with the wedge 7 rotatably disposed on a screw 15. A torque wrench 17 is used to apply a tightening force on the screw 15 generally in the range of 60 to 70 inch pounds, which translate to a given force on the wedge 7 that acts on the "V" shaped groove or notch 3 to spread the adjacent shroud portions 2. The screw 15 and wedge 7 are preferably lubricated to reduce friction and provide a uniform wedging force from a given applied torque.

The operation of the system is as follows: the lubricated wedge 7 is inserted into the notch 3 and the screw 15 is tightened with a torque wrench 17 applying a torque in the range of 60–70 inch pounds, which translates to a predetermined wedging force. A gap 11 opening is formed and the width of the gap 11 is measured with a feeler gauge 9. The width of the gap 11 and torque on the torque wrench are recorded. A shim having a thickness corresponding to the measured gap 11 is placed on the gap 11 and then the wedge 7 is removed and the same procedure is followed at each notch 3 around the periphery of the shroud.

Another method of measuring the tightness of the shroud portion of an array of integrally shrouded blades is made by opening the gap to receive a given thickness shim for example, a 0.002 inch shim, which is placed in the gap 11 and then the gap is closed by relieving the force on the C-clamp 13 clamping the shim tightly in the gap. A torque is slowly applied to the torque wrench 17 increasing the force wedging the shroud portions 2 apart until the shim can be pulled from the gap 11 utilizing a light force applied by hand. The force at which the shim can be pulled from the gap is also recorded. This procedure is repeated at each notch 3 around the periphery of the shroud. These measurements provide an indication of the tightness of the shroud and also provide a group of base measurements, which can be used with similar measurements made after the turbine has been in service and has come down for repair. By comparing the initial and subsequent measurements an indication of the wear of the shroud portions is obtained.

What is claimed is:

1. Method of checking the tightness of a shroud portion of a circular array of integrally shrouded turbine blades disposed in a turbine rotor comprising the steps of:
    forming each turbine blade so that it has a shroud portion made integral therewith;
    forming a notch in the shroud portion of the circular array of turbine blades at the juncture of two blades by removing corner portions of two adjacent blade shroud portions;
    providing spreading means which register with the notch for forcing the two adjacent blade shroud portions with the corners removed apart forming a gap therebetween when a force is applied to the spreading means;
    applying a predetermined force to the spreading means to form the gap between the two adjacent blade shroud portions that form the notch; and
    measuring the width of the gap formed by the predetermined force to obtain an indication of the tightness of the shroud portion of the circular array of blades when the blades are disposed in a turbine rotor.

2. The method as set forth in claim 1 and further comprising the steps of:
    recording the width of the gap formed by the predetermined force;
    applying the predetermined force to the spreading means to form a gap between the two adjacent blade shroud portions that form the notch at a later time;
    measuring and recording the width of the gap formed at the later time and comparing the later recorded width with the earlier recorded width to determine wear of the shroud portions.

3. The method set forth in claim 2 and further comprising the step of forming a notch which is generally "V" shaped.

4. The method as set forth in claim 1 and further comprising the step of forming a notch which is generally "V" shaped.

5. The method as set forth in claim 4 and further comprising the step of providing an opening at the converging end of the "V"-shaped notch to prevent the spreading means from bottoming out.

6. The method as set forth in claim 4 wherein the step of providing the spreading means comprises providing spreading means with a wedge shaped member which registers with and engages the "V" shaped notch.

7. The method as set forth in claim 4 wherein the step of providing spreading means comprises providing a wedge shaped member which registers with and engages the "V" shaped notch and has an apex portion of the wedge-shaped member removed.

8. The method as set forth in claim 1 and further comprising the step of providing a notch in the shroud portion of a plurality of adjacent shroud portions spaced at predetermined intervals about the circumferential array and measuring and recording the thickness of gaps formed at each notch by applying a predetermined spreading force to the spreading means at each notch.

9. The method as set forth in claim 8 and further comprising the steps of:
    providing a shim having a thickness equal to said thickness of the measured gap; and
    placing said shim having a thickness equal to said thickness of the measured gap, in the gap just measured, prior to forming and measuring a gap at the adjacent notch.

10. A method of checking the tightness of a shroud portion of a circular array of integrally shrouded turbine blades disposed in a turbine rotor comprising the steps of:
    forming each turbine blade so that it has a shroud portion made integral therewith;
    forming a notch in the shroud portion of the circular array of integrally shrouded turbine blades at the juncture of two blades by removing corner portions of two adjacent blade shroud portions;
    providing spreading means which register with the notch for forcing the two adjacent blade shroud portions forming the notch apart to form a gap therebetween;
    applying sufficient force to the spreading means to form a gap sufficiently wide to receive a shim of predetermined thickness;
    inserting said shim in said gap;
    reducing said force being applied to the spreading means in order to clamp said shim in the gap;
    increasing said force applied to the spreading means gradually until said shim can be pulled from the gap; and
    recording the force being applied when said shim can be pulled from the gap to provide an indication of the tightness of the shroud portion of the circular array of turbine blades disposed in a turbine rotor.

11. The method as set forth in claim 10 and further comprising the steps of:
    providing a sufficient force to the spreading means to form a gap sufficiently wide to receive said shim of predetermined thickness at a later time;
    inserting the shim of predetermined thickness into the gap at a later time;
    reducing the force applied to the spreading means to clamp the shim of predetermined thickness in the gap at a later time;
    increasing the force applied to the separating means until the shim of predetermined thickness can be pulled from the gap at a later time;
    measuring the force being applied when the shim of predetermined thickness can be pulled from the gap at a later time;
    recording the force being applied when the shim of predetermined thickness can be pulled from the gap at a later time and
    comparing the earlier recorded force with the later recorded force to provide an indication of wear between the shroud portions forming a totally integrated shroud.

12. The method as set forth in claim 10 and further comprising the step of providing a notch in the shroud portion of a plurality of adjacent shroud portions spaced at a predetermined interval about the circumferential array and measuring and recording the force applied when said shim of predetermined thickness can be pulled from the gap at each notch.

* * * * *